United States Patent
Znaiguia et al.

(10) Patent No.: US 9,187,395 B2
(45) Date of Patent: Nov. 17, 2015

(54) METHOD FOR PREPARING ACROLEIN FROM GLYCEROL

(71) Applicants: Adisseo France S.A.S., Antony (FR); Centre National de la Recherche Scientifque, Paris Cedex (FR); Universite Claude Bernard, Villeurbanne (FR)

(72) Inventors: Raja Znaiguia, Villeurbanne (FR); Jean-Marc Millet, Lyons (FR); Stéphane Loridant, Meyzieu (FR); Patrick Rey, Lyons (FR)

(73) Assignees: ADISSEO FRANCE S.A.S. (FR); CENTRE NATIONAL DE LA RECHERCHE SCIENTIFIQUE (FR); UNIVERSITE CLAUDE BERNARD (FR)

(*) Notice: Subject to any disclaimer, the term of this patent is extended or adjusted under 35 U.S.C. 154(b) by 0 days.

(21) Appl. No.: 14/437,707

(22) PCT Filed: Oct. 29, 2013

(86) PCT No.: PCT/FR2013/052582
§ 371 (c)(1),
(2) Date: Apr. 22, 2015

(87) PCT Pub. No.: WO2014/068241
PCT Pub. Date: May 8, 2014

(65) Prior Publication Data
US 2015/0239815 A1    Aug. 27, 2015

(30) Foreign Application Priority Data
Oct. 30, 2012    (FR) ..................................... 12 60358

(51) Int. Cl.
*C07C 45/52*    (2006.01)

(52) U.S. Cl.
CPC ...................................... *C07C 45/52* (2013.01)

(58) Field of Classification Search
None
See application file for complete search history.

(56) References Cited

U.S. PATENT DOCUMENTS

| 2008/0214384 A1 | 9/2008 | Redlingshofer et al. |
| 2011/0288323 A1 | 11/2011 | Belliere-Baca et al. |
| 2013/0197258 A1 | 8/2013 | Lauriol-Garbey et al. |

FOREIGN PATENT DOCUMENTS

WO   WO2011/157959 A1 * 12/2011 .............. C07C 45/52

OTHER PUBLICATIONS

International Search Report for International Application No. PCT/FR2013/052582, International Filing Date Oct. 29, 2013, Date of Mailing Apr. 8, 2014, 6 pages.

* cited by examiner

*Primary Examiner* — Brian J Davis
(74) *Attorney, Agent, or Firm* — Cantor Colburn LLP

(57) ABSTRACT

The disclosure concerns a method for preparing acrolein from glycerol, according to which a dehydration of the glycerol is carried out in the presence of a catalyst MWOA, wherein MWO represents a mixture of simple oxides and/or mixed oxides of tungsten and at least one metal M selected among zirconium, silicon, titanium, aluminium and yttrium, and A represents one or several Lewis base(s), one said Lewis base being of the formula $B(R1)_p(R2)_q(R3)_r$, wherein B is an element selected among C, S, P, O, N and halides, R1, R2 and R3 represent, independently of each other, H, a C1-C6 alkyl group, O, OH or OR wherein R represents a C1-C6 alkyl group, and the sum of p, q and r varies from 0 to 4.

14 Claims, No Drawings

METHOD FOR PREPARING ACROLEIN FROM GLYCEROL

CROSS REFERENCE TO RELATED APPLICATIONS

This is a U.S. national stage of application No. PCT/FR2013/052582, filed on 29 Oct. 2013. Priority under 35 U.S.C. §119(a) and 35 U.S.C. §365(b) is claimed from French Application No. 12/60358 filed on 30 Oct. 2012, the disclosure of which is also incorporated herein by reference.

The present invention concerns a catalytic method for manufacturing acrolein by dehydration of the glycerol and applications of such a method.

By glycerol, or glycerin, it is meant a glycerol, purified or not, from natural origin, resulting from the hydrolysis of vegetal oils and/or animal fats, or a glycerol from synthetic origin, derived from petroleum, more or less purified or refined, or crude. A purified glycerol has a degree of purity higher than or equal to 98%, obtained after distillation. A non-purified or only partially purified glycerol may be in a solution, in methanol and/or water, when it comes for example from a transesterification of triglycerides. In the following description, reference will be mainly made to the conversion of a biomass-derived glycerol, this is a preferred variant, but it goes without saying that the invention is not limited thereto and that its interest extends to all glycerols, regardless of their origins and degrees of purity.

There are known methods for converting glycerol into acrolein, by catalytic dehydration, according to the following reaction:

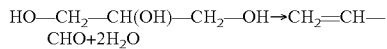

$$HO-CH_2-CH(OH)-CH_2-OH \rightarrow CH_2=CH-CHO+2H_2O$$

The glycerol (also called glycerin) has been known for a long time as a source of acrolein by thermal transformation, it is a product that is found widely in nature, in the form of esters (triglycerides), in particular in all animal or vegetable fats and oils, making it a starting reagent available in sufficient quantities, and thereby industrially usable. In fact, it is known that the glycerol decomposes to give acrolein when it is brought to temperatures higher than 280° C. This poorly selective reaction is accompanied with the formation of numerous by-products including acetaldehyde, hydroxyacetone, in addition to the total oxidation products CO, $CO_2$. Hence, it is essential to control the reaction of transformation of the glycerol into acrolein in order to avoid a useless waste of this resource and to proceed without an energetically costly later separation with a process for purifying the complex acrolein. Moreover, these impurities, essentially aromatic derivatives, are often the origin of the formation of coke at the surface of the catalyst which poisons the latter over time; it is often necessary to regenerate the catalyst in order to recover a satisfactory catalytic activity.

According to WO2010/076510A2, the dehydration of the glycerol into acrolein is carried out, in the presence of a catalyst which may consist of a silicon oxide and a mixed oxide of zirconium and tungsten or a titanium oxide and a mixed oxide of zirconium and tungsten; according to WO2011/157959A1, there is known a catalyst consisting of a zirconium oxide, a silicon oxide and a tungsten oxide, for performing this conversion. These conditions allow increasing the glycerol conversion rate, the acrolein selectivity and the stability over time of these properties. Nonetheless, these performances are not obtained quickly, sometimes only after 20 hours of reaction, and the need for a further more efficient catalyst is felt, especially faced to an ever increasing pressure of policies of rational exploitation of renewable materials.

The invention aims to remove the problems encountered with the known catalysts in the dehydration reaction of the glycerol into acrolein.

The object of the present invention consists of the implementation of catalysts which, while improving the abovementioned limitations, remain robust and regenerable, allowing to produce acrolein directly from glycerol, in particular biomass-derived glycerol.

Thus, this variant allows providing a competitive method for synthetizing acrolein from another renewable raw material, which does not depend on the propylene oil-derived resource.

This possibility is particularly advantageous for synthetizing methionine or its analogues, such as its hydroxy-analogue (HMTBA), directly from biomass.

Thus, the invention further relates to an application of this reaction to the synthesis of the 3-(methylthio)propionaldehyde (MTPA), the 2-hydroxy-4-methylthiobutyronitrile (HMTBN), the methionine and its analogues such as the 2-hydroxy-4-methylthiobutanoic acid (HMTBA) and the 2-oxo-4-methylthiobutanoic acid, as well as the metal chelates (Zn, Ca, Cr, Cu . . . ) and the esters of these acids, such as the isopropyl ester of HMTBA, from acrolein.

The methionine, the HMTBA, the esters and chelates thereof, and their analogues are used in animal nutrition and, in their processes for industrial synthesis, the acrolein is, in general, obtained by oxidation of propylene and/or propane. The oxidation of propylene into acrolein by air in the presence of water is partial, and the resulting crude product, based on acrolein, also contains propylene and propane which have not reacted, water and by-products of the oxidation reaction, in particular acids, aldehydes and alcohols.

Thus, the invention concerns a method for preparing acrolein from glycerol, in which a dehydration of the glycerol is carried out in the presence of a catalyst MWOA, wherein MWO represents a mixture of simple oxides and/or mixed oxides of tungsten and at least one metal M selected among zirconium, silicon, titanium, alumina and yttrium and A represents one or several Lewis base(s), one said Lewis base being of the formula B(R1)p(R2)q(R3)r, wherein B is an element selected among C, S, P, O, N and halides, R1, R2 and R3 represent, independently of each other, H, a C1-C6 alkyl group, O, OH or OR wherein R represents a C1-C6 alkyl group, and the sum of p, q and r varies from 0 to 4. In a variant of the invention, M represents at least two metals selected among zirconium, silicon, titanium, alumina and yttrium. M may also represent at least three or four of these metals, or even all of these five metals.

As it will appear from the examples, the supply of this or these Lewis base(s) to the aforementioned oxides mixtures allows significantly reducing the duration of the system layout, while maintaining a glycerol conversion rate, an acrolein selectivity and yield which are high over long time periods.

A representing one or several Lewis base(s), the value of the indexes p, q and r, the sum of which varies from 0 to 4, and which may thereby be equal to 0, 1, 2, 3 or 4, will be selected depending on the nature of the element B.

Appropriate Lewis bases are selected among phosphate anions, carbonates, carboxylates, sulfates, borates, alcoholates, alcohols and halides, as well as their mixtures. The preferred bases are those selected among phosphate ions $H_xPO_4^{(x-3)}$, x varying from 0 to 2, $H_3PO_4$, borate ions, and the halides $F^-$, $Cl^-$, $Br^-$, $I^-$, as well as their mixtures.

Advantageously, the surface molar ratio A/M varies from 0.005 to 0.5, still more preferably it varies from 0.015 to 0.09; A corresponding to the total quantity of Lewis bases.

The surface of the oxides of the catalyst is doped by the Lewis base. It may also be added at any time during the synthesis of the catalyst, and in particular during the synthesis or once the catalyst is formed. If several Lewis bases are added, they may be incorporated, respectively, at different steps or not, during the synthesis of the catalyst. As a complement and in order to preserve the catalytic performances of the thus prepared catalysts, these same doping agents may possibly be added via the supply of reagents during the operation of the reactor.

Regarding the oxides present in the catalyst, they are determined by a molar ratio W/sum of the elements M, different from W; this ratio varies preferably from 0.005 to 0.4, and still more preferably from 0.01 to 0.1.

The reaction according to the invention may be implemented in a gas phase or in a liquid phase, preferably in a gas phase. When the reaction is conducted in a gas phase, different process technologies may be used to supply the reagents, namely the fixed-bed process, the fluidized-bed process or the circulating fluidized-bed process. The supply of the different reagents, applied to the aforementioned reactors, may be done, individually or already in the form of pre-mixtures. We carry out at a pressure in the range of atmospheric pressure and, preferably, at a substantially higher pressure. In the two first processes, in the fixed-bed process or in the fluidized-bed process, the regeneration of the catalyst may be separate from the catalytic reaction. It may, for example, be done ex situ by the conventional regeneration methods, such as combustion in air or with a gas mixture containing molecular oxygen. According to the method of the invention, the regeneration may be done in situ because the temperatures and pressures at which the regeneration is done are close to the reaction conditions of the method.

As regards the method in a liquid phase, the reaction may be carried out in a conventional reactor for a reaction in a liquid phase on a solid catalyst, but also in a catalytic distillation-type reactor in view of the significant difference between the boiling points of the glycerol (290° C.) and the acrolein (53° C.). There may also be reasonably considered a method in a liquid phase at a relatively low temperature which allows for a continuous distillation of the produced acrolein, thereby limiting the consecutive reactions of degradation of the acrolein.

The experimental conditions of the reaction in a gas phase consist preferably of a temperature comprised between 250 and 400° C. at a pressure comprised between 1 and 10 bars. In a liquid phase, the reaction is carried out at a temperature between 150 and 350° C. and at a pressure which may range from 3 to 70 bars.

Another advantage of the method of the invention lies in the form of the starting glycerol which may be in pure form or partially purified or in a solution, in particular an aqueous solution. Advantageously, an aqueous solution of glycerol is used. In an aqueous solution, the concentration of the glycerol is preferably at least 1%, more preferably it varies from 10 to 50% by weight and preferably between 15 and 30% by weight in the reactor. The glycerol concentration should not be too high in order to avoid side-reactions which burden the acrolein yield, such as the formation of glycerol ethers or acetalization reactions between the produced acrolein and the non-converted glycerol. Moreover, the glycerol solution should not be too diluted, because of an unacceptable energy cost induced by the evaporation of the glycerol. In all cases, it is easy to adjust the concentration of the glycerol solution by partially or totally recycling the water produced by the considered reaction. The energy optimization across the synthesis tends to recover heat at the reaction outlet in order to vaporize the glycerol flow supplied to the reactor.

Another object of the invention is a method for manufacturing 3-(methylthio)propionaldehyde (MTPA), 2-hydroxy-4-methylthiobutyronitrile (HMTBN), methionine, 2-hydroxy-4-methylthiobutanoic acid (HMTBA), its metal chelates (Zn, Ca, Cr, Cu . . . ), and its esters, in particular the isopropyl ester, and the 2-oxo-4-methylthiobutanoic acid (KMB), its metal chelates (Zn, Ca, Cr, Cu . . . ), and its esters, from acrolein, which method comprises the step of dehydration of the glycerol into acrolein according to the invention. In comparison with the conventional method for manufacturing acrolein by controlled oxidation of propylene, the acrolein produced according to the aforementioned method may contain impurities which are different from the traditional method, in terms of their quantity as well as of their nature. Depending on the considered use, whether synthesis of acrylic acid or methionine or its hydroxy-analogue, it might be considered to purify the acrolein according to techniques known by those skilled in the art.

Thus, once the acrolein is directly obtained according to the invention, or after purification, it is reacted with methyl mercaptan (MeSH) in order to produce the 3-(methylthio) propionaldehyde (or MTPA). In a following step, the MTPA is brought into contact with the hydrocyanic acid in order to produce the 2-hydroxy-4-(methylthio)butyronitrile (HMTBN). After synthesis of the HMTBN, various reaction steps lead to methionine, its hydroxy-analogue (HMTBA), its metal chelates (Zn, Ca, Cr, Cu . . . ), and its esters, or its oxo-analogue (KMB), its metal chelates (Zn, Ca, Cr, Cu . . . ), and its esters. All these steps, starting from the synthesis of acrolein, are well known by those skilled in the art.

Another object of the invention is the use of a catalyst as previously defined, for converting the glycerol into acrolein.

The characteristics and advantages of the invention will appear from the examples hereinafter, illustrating catalysts of the invention, their method for obtaining them, as well as their performances in the reaction of conversion of glycerol into acrolein, in comparison with catalysts of the prior art.

The catalysts of the prior art, A, C, D and F are considered in the examples 1, 3, 4 and 7, respectively. The catalysts of the invention, B, E and G are considered in the examples 2, 5 and 8, respectively. The comparison of the performance between the catalysts A, C and D on the one hand, and the catalysts B and D on the other hand, is illustrated in the example 6 and the one between the catalyst F and the catalyst G is illustrated in the example 9.

Each of the catalysts A-G is characterized by the following parameters:

Its specific surface expressed in $m^2/g$ and measured by the BET method,

Its tungsten and metal M contents expressed by a molar ratio W/sum of the elements M, different from W, and measured by ICP-OES (Inductively Coupled Plasma-Optical Emission Spectroscopy).

The catalysts B, E and G are further characterized by the surface atomic ratio A/M measured by XPS (X-ray Photoelectron Spectroscopy); A corresponding to the total quantity of Lewis base(s).

The dehydration reaction of the glycerol is conducted on the indicated catalysts, at atmospheric pressure or at a substantially higher pressure, in a straight fixed-bed reactor. The reactor is placed in an oven which allows keeping the catalyst at the reaction temperature which is of 300° C. The reactor is supplied with an aqueous solution at 20% by weight of glycerol. The aqueous solution of glycerol is vaporized thanks to a C.E.M. (Controlled Evaporator Mixer) evaporator Bronkhorst® in the presence of a nitrogen flow rate. The relative molar proportion glycerol/water/nitrogen is of 2.3/46.3/51.4. The GHSV (Hourly space Velocity) is defined as follows:

$$GHSV = (\text{total molar flow rate} \times \text{Temperature} \times R)/(\text{Catalyst volume} \times \text{Patm})$$

Wherein Patm=101325 Pa, Temperature=25° C. and the total molar flow rate=molar flow rate of the glycerol+molar flow rate of water+molar flow rate of the inert gas.

EXAMPLE 1

Preparation and Characterization of the Catalyst A (Prior Art)

The catalyst A is of the type tungstated zirconia doped with silica, that is to say a catalyst consisting of a mixture of zirconium oxide, tungsten oxide and silicon oxide.

The preparation of this solid includes the following three steps.

The first step is the synthesis of the hydrated zirconium hydroxide by co-precipitation of a solution of zirconium oxynitrate $ZrO(NO_3)_2 \cdot xH_2O$ (Aldrich, >99%) and an ammonia solution at 28% and at pH=8.8.

The second step consists in stabilizing the hydrated zirconium hydroxide by silicic species by addition of a solution of tetra-ethyl-ortho-silicate, TEOS, $Si(OC_2H_5)_4$ (Aldrich, 99,999%). The hydrated zirconium hydroxide is placed in a Teflon flask containing an ammoniacal solution the pH of which is adjusted to 12 (molar ratio Si/Zr=0.01). The mixture is stirred for 24 h then filtered and washed with deionized water.

The last step is the exchange with the tungstic acid $H_2WO_4$ (Aldrich, 99%) dissolved in a hydrogen peroxide at 35% at 50° C. The concentration of the tungstic acid solution is of 0.1M. The tungstic acid solution is then cooled to ambient temperature, and the zirconium hydroxide doped with silica is added slowly. The obtained solid is filtered then calcined in air at 750° C.

Its specific surface is of about 55 $m^2/g$. The molar composition W/M of this catalyst is of 3.5/96.5.

EXAMPLE 2

Preparation and Characterization of the Catalyst B (Invention)

A catalyst of the type tungstated zirconia doped with silica and phosphorus, that is to say a catalyst consisting of a mixture of zirconium oxide, tungsten oxide and silicon oxide and a phosphate-based Lewis base, is prepared according to the invention. It is synthesized with the same protocol as that of the catalyst A but, after calcination of the solid, the phosphorus is added by impregnation in excess from a solution of $H_3PO_4$ (Aldrich, >99%) at 0.2M (molar ratio P/Zr=0.04). The mixture is stirred for 24 h then filtered, washed with deionized water and dried.

Its specific surface is of about 55 $m^2/g$. Its molar composition W/M is identical to that of the catalyst A.

The surface atomic ratio A/M is of 0.09 (with A representing the phosphate-based Lewis base).

EXAMPLE 3

Preparation and Characterization of the Catalyst C (Prior Art)

The catalyst C is a tungstated zirconia, namely a mixture of zirconium oxide and tungsten oxide, synthesized by Daiichi Kigenso (supplier reference: Z-1104).

The specific surface of this catalyst is of 77 $m^2/g$ and its molar composition W/M is of 3.3/96.7.

EXAMPLE 4

Preparation and Characterization of the Catalyst D (Prior Art)

The catalyst D is of the type tungstated zirconia doped with silica, that is to say it consists of a mixture of zirconium oxide, tungsten oxide and silicon oxide. The preparation of this solid includes the same steps as those of the catalyst A, with the exception of the tungsten content.

Its specific surface is of 63 $m^2/g$. Its molar composition W/M is of 4.1/95.9.

EXAMPLE 5

Preparation and Characterization of the Catalyst E (Invention)

A catalyst of the type tungstated zirconia doped with silica and phosphorus, that is to say a catalyst consisting of a mixture of zirconium oxide, tungsten oxide and silicon oxide and a phosphate-based Lewis base, is prepared according to the invention. It is synthesized with the same protocol as that of the catalyst D but, after calcination, the phosphorus is added by impregnation in excess from a solution of $H_3PO_4$ (Aldrich, >99%) at 0.2M (P/Zr=0.04). The mixture is stirred for 24 h then filtered, washed with deionized water and dried.

Its specific surface is of 63 $m^2/g$. Its molar composition W/M is identical to that of the catalyst D.

The surface atomic ratio A/M is of 0.09 (with A representing the phosphate-based Lewis base).

EXAMPLE 6

Evaluation of the Catalysts a, B, C, D and E in the Catalytic Dehydration of the Glycerol into Acrolein The table 1 gives the performances obtained with the catalysts A, B, C, D and E at different reaction times. The catalysts A, B, D and E have been evaluated with a GHSV (Gas Hourly Space Velocity) of 2900 $h^{-1}$ in contrast with 1930 $h^{-1}$ for the catalyst C.

TABLE 1

| | Catalyst | | | | | | | | | | | | | | |
|---|---|---|---|---|---|---|---|---|---|---|---|---|---|---|---|
| | A (comparative) | | | B (invention) | | | C (comparative) | | D (comparative) | | | E (invention) | | | |
| | GHSV (h-1) | | | | | | | | | | | | | | |
| | 2900 | | | 2900 | | | 1930 | | 2900 | | | 2900 | | | |
| | Reaction time (h) | | | | | | | | | | | | | | |
| | 5 | 24 | 48 | 5 | 24 | 48 | 6 | 27 | 3 | 24 | 54 | 5 | 26 | 54 | |
| Glycerol conversion | 100 | 99 | 96 | 100 | 97 | 91 | 94 | 77 | 100 | 100 | 87 | 98 | 93 | 91 | |
| Acrolein selectivity | 35 | 68 | 66 | 72 | 75 | 68 | 64 | 68 | 38 | 54 | 42 | 71 | 80 | 78 | |
| Acrolein yield | 35 | 68 | 63 | 72 | 73 | 61 | 60 | 53 | 38 | 54 | 37 | 70 | 75 | 71 | |
| Acetaldehyde yield | 2.4 | 2.3 | 1.4 | 2.7 | 1.8 | 1.1 | 3.8 | 2.3 | 4.1 | 2.4 | 1.7 | 3.9 | 2.9 | 1.8 | |
| Propionaldehyde yield | 1.7 | 1.1 | 0.7 | 3.1 | 2.2 | 1.6 | 2.8 | 1.9 | 2.1 | 1.4 | 1.0 | 2.8 | 2.6 | 1.5 | |
| Acetone yield | 1.2 | 1.2 | 1.2 | 1.0 | 0.9 | 0.7 | 1.5 | 1.4 | 1.9 | 1.7 | 1.6 | 1.3 | 1.5 | 1.2 | |
| Allylalcohol yield | 1.3 | 0.8 | 0.8 | 0.6 | 0.9 | 0.9 | 0.4 | 0.6 | 0.0 | 0.2 | 0.9 | 0.7 | 1.0 | 1.1 | |
| Hydroxyacetone yield | 2.5 | 9.0 | 10.7 | 6.8 | 9.5 | 8.8 | 6.0 | 6.5 | 1.1 | 9.3 | 9.6 | 5.2 | 6.2 | 11.8 | |
| Phenol yield | 1.1 | 0.1 | 0.1 | 0.9 | 0.2 | 0.0 | 0.8 | 0.2 | 1.5 | 0.2 | 0.0 | 3.2 | 0.9 | 0.2 | |

The catalysts A, B, D and E allow for a total (or an almost total) conversion of the glycerol at 5 h, and are considerably more stable than the catalyst C despite of the use of a greater GHSV. The catalysts B and E (according to the invention) allow obtaining better acrolein selectivities at 24 h. In addition, they are quickly selective (at 5 h) and remain so until 48-54 h.

EXAMPLE 7

Preparation and Characterization of the Catalyst F
(Prior Art)

The catalyst F is of the type tungstated zirconia doped with silica, that is to say a catalyst comprising a mixture of zirconium oxide, tungsten oxide and silicon oxide. The preparation of this solid includes the same steps as those of the catalyst A, with the exception of the calcination temperature. Indeed, the solid obtained after addition of tungsten, filtration and drying is calcined in air at 650° C. instead of 750° C.

Its specific surface is of 153 m²/g. Its molar composition W/M is of 11.8/88.2.

EXAMPLE 8

Preparation and Characterization of the Catalyst G
(Invention)

A catalyst of the type tungstated zirconia doped with silica, phosphorus and fluorine, that is to say a catalyst comprising a mixture of zirconium oxide, tungsten oxide and silicon oxide and two Lewis bases, one based on phosphate and the other based on fluorine, is prepared according to the invention. It is prepared with the same protocol as that of the catalyst F. The only difference for this catalyst is that it is treated in a Teflon flask containing an ammoniacal solution the pH of which is adjusted to 11.9. The mixture is stirred for 24 h without addition of TEOS, then filtered and washed with deionized water. The used equipment and this treatment are responsible for the doping of the solid with phosphate and fluorine ions.

Its specific surface is of 91 m²/g. Its molar composition W/M is of 4.5/95.5.

The surface atomic ratio P/M is 0.02. The surface atomic ratio F/M is 0.004, which gives a surface atomic ratio A/M of 0.06, M representing Zr and Si.

EXAMPLE 9

Catalytic Dehydration of the Glycerol into Acrolein:
Evaluation of the Catalysts F and G The table 2 gives the performances obtained with the catalysts F and G at different reaction times.

TABLE 2

| | F (comparative) | | | G (invention) | | |
|---|---|---|---|---|---|---|
| | GHSV (h-1) | | | | | |
| | 2175 | | | 2900 | | |
| | Reaction time (h) | | | | | |
| | 4 | 24 | 40 | 5 | 24 | 44 |
| Glycerol conversion | 100 | 100 | 100 | 100 | 100 | 99 |
| Acrolein selectivity | 60 | 69 | 71 | 73 | 76 | 79 |
| Acrolein yield | 60.2 | 69.4 | 70.8 | 72.9 | 75.7 | 78.5 |
| Acetaldehyde yield | 4.0 | 3.8 | 3.0 | 3.8 | 2.4 | 2.2 |
| Propionaldehyde yield | 6.7 | 2.8 | 2.2 | 3.3 | 2.2 | 2.4 |
| Acetone yield | 4.4 | 2.7 | 2.3 | 2.2 | 1.9 | 1.4 |
| Allylalcohol yield | 0.2 | 0.4 | 0.4 | 0.2 | 0.7 | 1.1 |
| Hydroxyacetone yield | 0.3 | 6.5 | 8.8 | 3.8 | 7.9 | 11.2 |
| Phenol yield | 0.3 | 1.8 | 0.1 | 0.6 | 0.3 | 0.1 |

The catalysts F and G allow obtaining similar stabilities. In contrast, the catalyst G, doped with phosphate and fluorine ions (according to the invention), allows obtaining better selectivities (up to 79%) even after only 4 h of test.

The invention claimed is:

1. A method for preparing acrolein from glycerol, characterized in that a dehydration of the glycerol is carried out in the presence of a catalyst MWOA, wherein MWO represents a mixture of simple oxides and/or mixed oxides of tungsten and at least one metal M selected among zirconium, silicon, titanium, aluminium and yttrium, and A represents one or several Lewis base(s), one said Lewis base being of the formula B(R1)p(R2)q(R3)r, wherein B is an element selected among C, S, P, O, N and halides, R1, R2 and R3 represent, independently of each other, H, a C1-C6 alkyl group, O, OH or OR wherein R represents a C1-C6 alkyl group, and the sum of p, q and r varies from 0 to 4.

2. The method according to claim 1, characterized in that M represents at least two or three metals selected among zirconium, silicon, titanium, aluminium and yttrium.

3. The method according to claim 1, characterized in that A is selected among phosphate ions $H_xPO_4^{(x-3)}$, x varying from 0 to 2, $H_3PO_4$, borate ions, $F^-$, $Cl^-$, $Br^-$, $I^-$, $NH_3$, $CN^-$, sulfate ions, carbonate ions, carboxylate ions, alcohols, alcoholate ions, as well as their mixtures.

4. The method according to claim 1, characterized in that the surface molar ratio A/M varies from 0.005 to 0.5.

5. The method according to claim 4, characterized in that said surface molar ratio varies from 0.015 to 0.09.

6. The method according to claim 1, characterized in that the molar ratio W/sum of the elements M, different from W, varies from 0.005 to 0.4.

7. The method according to claim 6, characterized in that said molar ratio varies from 0.01 to 0.1.

8. The method according to claim 1, characterized in that the glycerol is in an aqueous solution, in a concentration of at least 1% by weight.

9. The method according to claim 8, characterized in that the glycerol concentration of the aqueous solution varies from 10 to 50% by weight.

10. The method according to claim 1, characterized in that the catalyst is regenerated.

11. A method for manufacturing the 3-(methylthio)-propionaldehyde MTPA, the 2-hydroxy-4-methylthiobutyronitrile HMTBN, the methionine, the 2-hydroxy-4-methylthiobutanoic acid HMTBA, the esters and the metal chelates thereof, or the 2-oxo-4-methylthiobutanoic acid KMB, the esters and the metal chelates thereof, characterized in that it implements a method according to claim 1.

12. The method according to claim 1, characterized in that the dehydration reaction is carried out in a gas phase.

13. The method according to claim 12, characterized in that the dehydration reaction is carried out in a fixed-bed, fluidized-bed or circulating fluidized-bed reactor.

14. The method according to claim 1, characterized in that the dehydration reaction is carried out in a liquid phase.

* * * * *